(12) United States Patent  (10) Patent No.: US 9,375,348 B2
Gunn  (45) Date of Patent: Jun. 28, 2016

(54) SYSTEMS AND METHODS FOR A MEMBRANE-FREE ELECTROLYSIS PUMP FOR AN INTRAOCULAR IMPLANT

(71) Applicant: NOVARTIS AG, Basel (CH)

(72) Inventor: Nicholas M. Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 200 days.

(21) Appl. No.: 14/181,851

(22) Filed: Feb. 17, 2014

(65) Prior Publication Data

US 2015/0230984 A1 Aug. 20, 2015

(51) Int. Cl.
*A61M 5/00* (2006.01)
*A61F 9/007* (2006.01)
*F04B 43/04* (2006.01)
*F04B 19/00* (2006.01)

(52) U.S. Cl.
CPC ........... *A61F 9/00781* (2013.01); *F04B 19/006* (2013.01); *F04B 43/043* (2013.01)

(58) Field of Classification Search
CPC .............. A61F 9/00781; A61F 9/0017; A61F 2240/001; A61B 3/16; A61B 5/0084; A61M 27/00; A61M 2210/0612; B01L 3/502707; H01M 8/04201; F04B 37/06; F04B 43/043; F04B 19/006
USPC .................. 604/8, 9; 417/48–51, 393, 395
See application file for complete search history.

(56) References Cited

U.S. PATENT DOCUMENTS

| 6,168,575 | B1 | 1/2001 | Soltanpour |
| 8,891,949 | B2 * | 11/2014 | Hong ................. F04B 19/006 392/471 |
| 2002/0114715 | A1 | 8/2002 | Yoon et al. |
| 2008/0118790 | A1 * | 5/2008 | Kim ..................... F04B 19/006 417/209 |
| 2008/0280112 | A1 * | 11/2008 | Langereis ......... B01L 3/502707 428/201 |
| 2009/0240215 | A1 | 9/2009 | Humayun et al. |
| 2012/0148931 | A1 * | 6/2012 | Kim .................. H01M 8/04201 429/443 |

OTHER PUBLICATIONS

Lee, J. et al, "Liquid Micromotor Driven by Continuous Electrowetting", Proceedings of MEMS'98, 11th IEEE International Workshop Micro Electromechanical System, Heidelberg, Germany, Jan. 25-29, 1998, pp. 538-543.

* cited by examiner

*Primary Examiner* — Philip R Wiest
(74) *Attorney, Agent, or Firm* — Kenneth D. Bassinger

(57) ABSTRACT

A microfluidic pump for implantation proximate an eye of a patient is provided herein. The pump includes a first substrate portion and a second substrate portion adjacent the first and a chamber that has a bottom surface and a top surface provided by the first and second substrate portions. A gas is produced within the chamber so that it displaces fluid from the chamber. The pump also includes an inlet channel and an outlet channel coupled to the chamber, the inlet channel being separated from the chamber by a first gap and the outlet channel separated from the chamber by a second gap. The gaps inhibit the gas from moving out of the chamber. Other microfluidic pumps and intraocular devices are also disclosed.

15 Claims, 5 Drawing Sheets

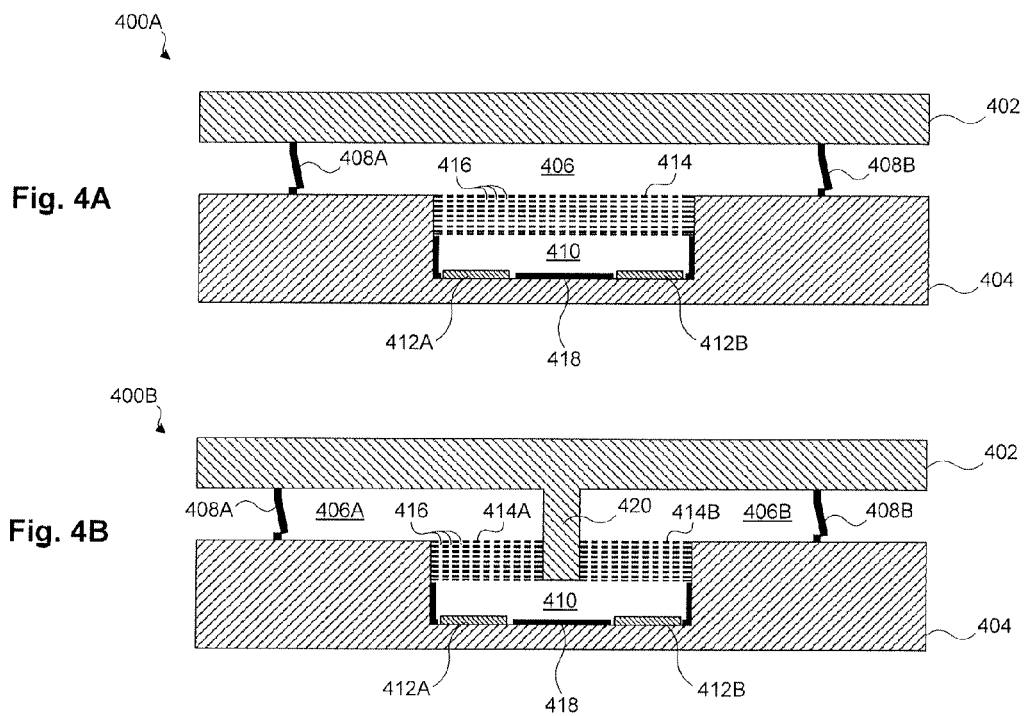

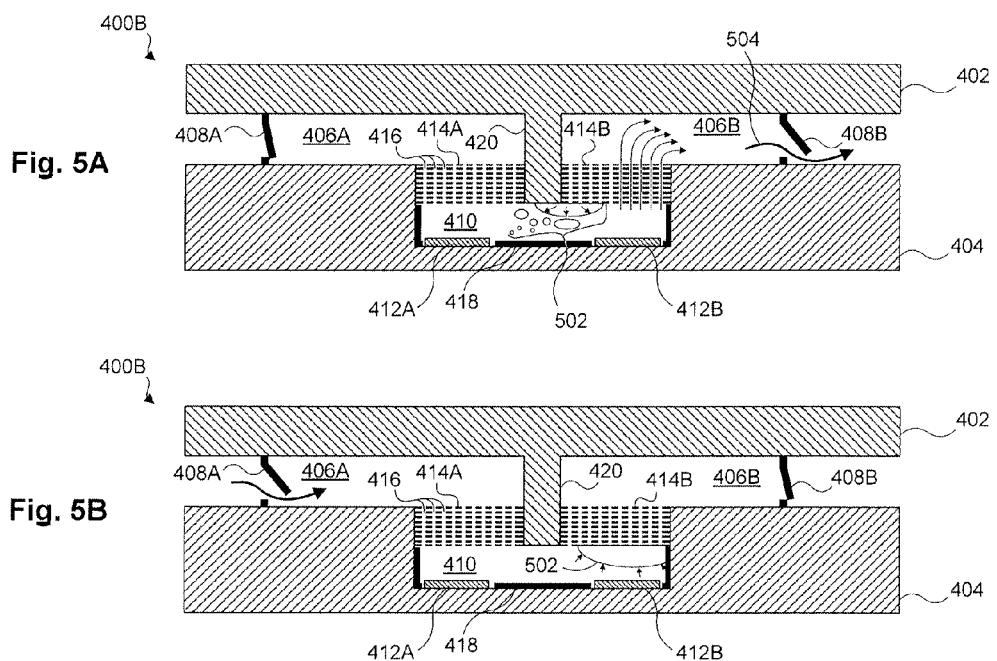

SYSTEMS AND METHODS FOR A MEMBRANE-FREE ELECTROLYSIS PUMP FOR AN INTRAOCULAR IMPLANT

BACKGROUND

The present disclosure relates generally to microfluidic pump systems and methods for ophthalmic treatments. More particularly, the present disclosure relates to microfluidic pump systems that may be used to drain fluid from an eye to alleviate elevated intraocular pressure (IOP).

Glaucoma, a group of eye diseases affecting the retina and optic nerve, is one of the leading causes of blindness worldwide. Most forms of glaucoma result when the IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye 100 that helps to explain the processes of glaucoma. In FIG. 1, representations of the lens 110, cornea 120, iris 130, ciliary body 140, trabecular meshwork 150, Schlemm's canal 160, and the edges of the sclera 170 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 180. The edge of the anterior chamber, which extends circumferentially around the eye, contains structures that allow the aqueous humor SY to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber 180. The sclera 170, the white of the eye, connects to the cornea 120, forming the outer, structural layer of the eye. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

As part of a method for treating glaucoma, a doctor may implant an intraocular device in or proximate a patient's eye. The intraocular device may monitor the pressure in a patient's eye and facilitate control of that pressure by allowing excess aqueous humor be drained from the anterior chamber of the eye to relieve the pressure in the eye, lowering IOP. Under certain conditions, the drainage site may become obstructed or pressurized. Such circumstances may lead to an undesired reduction or cessation of drainage of aqueous humor, leading to an elevated pressure within the anterior chamber of the eye that is potentially harmful.

The system and methods disclosed herein overcome one or more of the deficiencies of the prior art.

SUMMARY

In one exemplary aspect, the present disclosure is directed to a microfluidic pump for implantation proximate an eye of a patient. The microfluidic pump includes a first substrate portion and a second substrate portion adjacent to the first substrate portion. The microfluidic pump includes a channel that is defined by and between the first and second substrate portions and has a proximal end and a distal end. The channel has a first valve in the proximal end and a second valve in the distal end. The microfluidic pump also includes a chamber with a bottom surface, side surfaces, and a top surface. The top surface of the chamber is provided by a rigid, liquid-permeable wall. The chamber produces a gas that displaces fluid within the chamber and within the channel.

In another exemplary aspect, the present disclosure is directed to another microfluidic pump for implantation proximate an eye of a patient. The microfluidic pump includes a first substrate portion adjacent to a second substrate portion. The microfluidic pump also includes a chamber that has a bottom surface and a top surface provided by the first and second substrate portions. A gas that displaces fluid from the chamber is produced within the chamber. The pump further includes an inlet channel and an outlet channel coupled to the chamber. The inlet channel is separated from the chamber by a first gap, and the outlet channel is separated from the chamber by a second gap. The first and second gaps inhibit the gas from moving out of the chamber. The pump also includes a first valve in the inlet channel and a second valve in the outlet channel.

In yet another exemplary aspect, the present disclosure is direct to an intraocular device for regulating pressure within an eye of a patient. The intraocular device includes a plate with a cavity therein and a microfluidic pump configured with the cavity. The intraocular device also includes a flexible tube having a proximal end and a distal end, the proximal end being configured to insert into an anterior chamber of the eye. The distal end is coupled to the plate. The microfluidic pump includes a first substrate portion adjacent to a second substrate portion and a channel defined by and between the first and second substrate portions and in communication with the flexible tube. The pump includes a chamber having a bottom surface, side surfaces, and a top surface, wherein the top surface is provided by a liquid-permeable wall. A gas is produced within the chamber that displaces fluid from within the chamber into the channel and out of the pump.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

FIG. 4A is a cross-sectional view of a microfluidic pump according to exemplary aspects of the present disclosure.

FIG. 4B is a cross-sectional view of an alternative microfluidic pump of according to exemplary aspects of the present disclosure.

FIGS. 5A and 5B are cross-sectional views of the microfluidic pump of FIG. 4B in two different stages in a pumping process according to exemplary aspects of the present disclosure.

Figure 1:
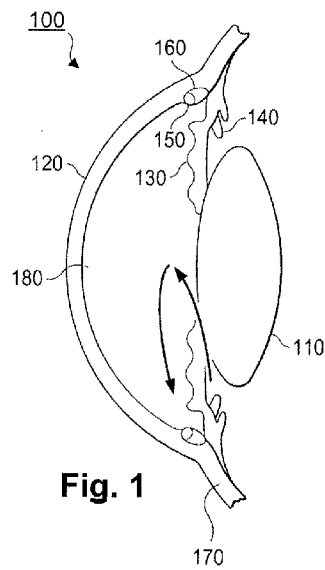
FIG. 1 is a cross-sectional view of the front portion of an eye.

Aspects of the accompanying drawing may not be drawn to scale. Individual features may be scaled larger or smaller relative to other features in order to better describe the features and exemplary aspects of the present disclosure. The drawings are better understood by reference to the following description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for maintaining a desired intraocular pressure in an eye of a patient by using an intraocular device that contains a microfluidic pump. In some aspects described herein, the microfluidic pump includes one or more microfluidic actuators coupled to a flow path that drains fluid from the anterior chamber 180 of the eye 100, even when a pressure is exerted within a drainage bleb or there is other resistance to the desired drainage. The systems and methods disclosed herein may enable better control and maintenance of intraocular pressure, potentially providing more effective treatment and greater customer satisfaction. In some aspects, the intraocular device is an intraocular pressure (IOP) controlling device, such as a glaucoma drainage device (GDD) that alleviates elevated IOP in a patient's eye.

Figure 2:
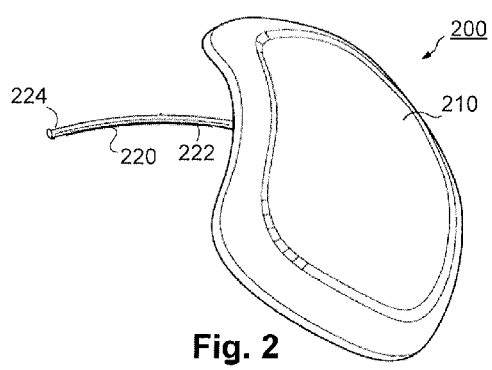
FIG. 2 is a perspective view of an intraocular implant device that carries a microfluidic pump according to an exemplary aspect of the present disclosure.
Figure 3:
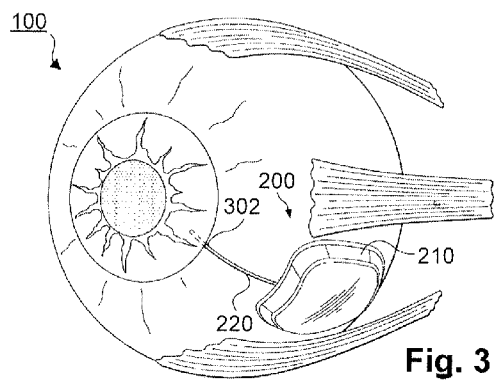
FIG. 3 is a perspective view of an intraocular implant device as situated proximate an eye according to an exemplary aspect of the present disclosure.

FIG. 2 is a schematic diagram of an intraocular implant or device 200 useable in the monitoring and treatment of a patient's eye. As depicted, the intraocular device 200 is a GDD. The intraocular device 200 includes a body referred to herein as a plate 210 with a first drainage tube 220 that extends from the plate 210. The first drainage tube 220 includes a proximal end portion 222 that couples the tube to one or more structures internal to the plate 210, such as a microfluidic pump as will be described herein. A distal end portion 224 of the first drainage tube 220 may be coupled to the eye of a patient to allow for the monitoring of pressure and/or the drainage of fluid. Embodiments of the intraocular device 200 may include additional tubes for priming and/or for the detection of pressure at other locations. FIG. 3 is a schematic diagram of an eye 100 (the anterior portion of which is shown in cross-section in FIG. 1) of a patient whose IOP is being monitored and who is receiving treatment with the intraocular device 200. The intraocular device 200 may be a GDD as depicted in FIG. 2. The plate 210 may include or be arranged to carry various components of an IOP control system, including for example, one or more of a power source, a processor, a memory, a data transmission module, and a flow control mechanism (e.g., a pump system). It may also carry one or more pressure sensor systems, including one or more pressure sensors, to monitor the pressures in and around the eye, including an intraocular pressure. This pressure may be used by other systems within the intraocular device 200, such as drainage systems used to regulate the intraocular pressure.

The plate 210 is configured to fit at least partially within the subconjunctival space and is sized within a range between about 15 mm×12 mm to about 30 mm×15 mm and has a thickness less than about 2 mm thick, preferably less than about 1 mm thick. The plate 210 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

In some embodiments, the first drainage tube 220 extends from an anterior side of the plate 210 and is sized and arranged to extend into the anterior chamber 180 (as seen in FIG. 1) of the eye through a surgically formed opening 302 in the sclera. The first drainage tube 220 is used to facilitate drainage and may also permit the measure of pressure within the anterior chamber 180. The first drainage tube 220 includes a first open end that may be disposed at a location where pressure measurements may be desired (in this instance within the anterior chamber 180) and from which fluid is drained, and at least one lumen that extends to a second open end that is disposed within or connected to the plate 210. Prior to placement around a patient's eye as depicted in FIG. 3, a chamber within the plate 210 may be primed by the injection of liquid that displaces a gas from the chambers, channels, and/or valves within the device 200. The liquid may be injected through the tube 220 until some liquid may exit through an outlet. In some embodiments, the fluid entering the device 200 through the first drainage tube 220 may be drained through a drain integrated into the plate 210, which may be positioned within a bleb (not shown).

FIG. 4A is a cross-sectional view of a microfluidic pump 400A that may be used to pump aqueous humor from an eye of a patient. The microfluidic pump 400A may be enclosed within a cavity within the plate 210 of FIGS. 2 and 3. As illustrated, the microfluidic pump 400A includes a first substrate portion 402 and a second substrate portion 404. The first and second substrate portions 402 and 404 may be made from glass, silicon, or a polymer such as silicone, Parylene, and polyimide. Other materials are also contemplated. In some embodiments, the first substrate portion 402 is made from a first material, and the second substrate portion 404 is made from a second material.

In some embodiments, the first and second substrate portions 402 and 404 are configured adjacent to each other and are coupled together. In other embodiments, they are formed as a unitary component, with some separation provided by a channel 406 between them. As illustrated the substrate portion 402 provides an upper bound to the channel 406, while the substrate portion 404 provides a lower bound thereto. The channel 406 includes a proximal portion that contains a first valve 408A and a distal portion that contains a second valve 408B. The valves 408A and 408B are check valves that permit fluid flow in one direction and stop it in another. Thus, fluid may flow through the channel 406 in the direction from the valve 408A toward the valve 408B, but the valves 408A and 408B both prevent flow from valve 408B toward valve 408A. The proximal portion of the channel 406 may be coupled to the proximal end 224 of the drainage tube 220 as seen in FIGS. 2 and 3. Thus, the fluid flowing through the channel 406 may be aqueous humor being drained from the anterior chamber 180 of the eye 100 of FIG. 1.

In some instances, a drainage path used to drain the aqueous humor may become impeded. For example, if pressure at the drainage site inhibits flow to the site or tissue obstructs the end of a drainage tube such as the drainage tube 230, a desired rate of drainage may become difficult to achieve. In order to forcefully pump the aqueous humor, the pump 400 includes a chamber 410 situated within the second substrate portion 404. In some embodiments, the chamber 410 is provided within the first substrate portion 402.

The chamber 410 has bottom, top, and side surfaces. The bottom surface of the chamber 410 includes a plurality of electrodes. As illustrated, the plurality of electrodes includes a first electrode 412A and a second electrode 412B. The top surface of the chamber 410 is provided by a semi-permeable wall 414. As illustrated the semi-permeable wall 414 includes a plurality of micro-pores 416. The micro-pores 416 are small holes extending through the wall 414 of the top surface. In some embodiments, the micro-pores 416 are laser drilled through the wall 414. The diameter of each of the micro-pores 416 and the thickness of the semi-permeable wall 414 is such that a fluid, such as aqueous humor, can run through the micro-pores, while a gas is inhibited from passing therethrough. For example, the micro-pores may range in diameter from about 1 micron to about 200 microns and the thickness of semi-permeable wall 414 may range from about 10 microns to 500 microns, but other sizes and arrangements are used in other embodiments.

Additionally, the wall 414 is formed by a hydrophilic material or may have a hydrophilic coating or surface. The dimensions of the micro-pores 416 that effectively prevent the passage therethrough of gas may depend on the degree of hydrophilicity of the semi-permeable wall 414. In general, less hydrophilic material may require pores of smaller diameter and/or greater length. In some embodiments, the process of laser-drilling the micro-pores generates a hydrophilic surface. The chamber 410 also includes a chamber lining provided by a recombination layer 418 formed over at least some of the bottom and side surfaces of the chamber 410. In some embodiments, the recombination layer 418 may be in contact within one of the first and second electrodes 412A and 412B. In other embodiments, the recombination layer 418 may provide one of the electrodes 412A and 412B.

As will be discussed in more detail herein, when an electric potential is applied within the chamber 410 by the electrodes 412A and 412B, a portion of the fluid within the chamber is transformed into a gas. For example, when aqueous humor is filling the chamber 410, an electrolysis process separates the water in the aqueous humor into hydrogen gas ($H_2$) and oxygen gas ($O_2$). As water is converted into gas, fluid within the chamber 410 is forced through the wall 414, which is permeable to the fluid but impermeable to gas. After the electric potential is removed, the recombination layer 418 facilitates the recombination of $H_2$ and $O_2$ into water. Additionally, some of the gas may dissolve into the remaining fluid. To the extent that the gases recombine into liquid and dissolve into the fluid, additional fluid enters the chamber 410. As the electric potential is cycled on and off, a cycle of expelling fluid from the chamber 410 and refilling the chamber 410 results. The valves 408A and 408B permit this cycling to force fluid in the permitted direction (from valve 408A toward valve 408B), as is described in more detail herein, thereby pumping fluid through the pump 400A.

FIG. 4B shows a cross-section of a microfluidic pump 400B that is similar in many respects to the microfluidic pump 400A shown in FIG. 4A. The pump 400B includes a first substrate portion 402 and a second substrate portion 404 as seen in FIG. 4A. The pump 400B further includes a dividing member 420. As illustrated, the dividing member 420 is a protrusion of the first substrate portion 402. The dividing member 420 bisects the channel 406 into a channel 406A comprising the distal portion of the channel 406 and a channel 406B comprising the proximal portion of the channel 406. The dividing member 420 also divides the semipermeable wall 414 into two portions, a wall portion 414A and a wall portion 414B.

Because of the dividing member 420, fluid is directed through the wall 414A into the chamber 410, which is filled with the fluid before the fluid passes through the wall 414B. The direction provided by the dividing member 420 may facilitate the removal of air pockets from the chamber 410 prior to use in pumping fluid through the pump 400B. The presence of air pockets not produced by the electrolysis process may decrease the performance of a microfluidic pump, such as pumps 400A and 400B.

In both the pumps 400A and 400B of FIGS. 4A and 4B, respectively, the semipermeable wall 414 (and walls 414A and 414B) may be provided by several structures. As described, the wall 414 may be provided by a plurality of laser-drilled micro-pores. Additional embodiments of the semipermeable wall 414 may be provided by a porous foam material. For example, the semipermeable wall 414 may be provided by an open-cell foam material that effectively comprises a plurality of micro-pores by nature of the material, rather than, or in addition to, by processing. Additional materials may be used that, by virtue of their mechanical or chemical structure are permeable to liquid but not to air.

FIGS. 5A and 5B show the pump 400B is two stages of a pumping process. In FIG. 5A, an electric potential is applied to the electrodes 412A and 412B within the chamber 410. The electric potential is applied as part of an electrolysis process by which water molecules within the chamber 410 are separated by the presence of a direct electric current induced by the potential into hydrogen gas ($H_2$) and oxygen gas ($O_2$). The gaseous hydrogen and oxygen forms bubbles 502 within the chamber 410. As the combined volume of the bubbles 502 increases, fluid is displaced out of the chamber 410. As the fluid is displaced, pressure within the chamber 410 and the channels 406A and 406B increases. The increase in pressure within the channel 406A closes the first valve 408A, preventing fluid from flowing out through the channel 406A, which prevents fluid from passing through the wall 414A. In contrast, the increase in pressure in the channel 406B opens the second valve 408A as indicated by the flow arrow 504, which indicate the flow of aqueous humor in the channel 406B. Thus, the electrolysis process introduces pressure that opens the second valve 408B and closes the first valve 408A pushing fluid out of the pump 400B.

In FIG. 5B, a second stage of the pumping process performed by pump 400B is shown. The electric potential provided to electrodes 412A and 412B is removed. The bubbles 502 (shown in FIG. 5B as a consolidated bubble) containing hydrogen and oxygen gas begin to decrease as the hydrogen and oxygen recombine to form water. The recombination layer 418 facilitates the recombination. As illustrated, the recombination layer 418 is formed from platinum, but may be formed from other metals or other materials in other embodiments. Additionally, some of the gas may dissolve into the fluid in the chamber 410, allowing some of it to pass through the wall 414B. As the volume occupied by the bubbles 502 decreases, the pressure within the chamber 410 decreases. This decrease in pressure closes the second valve 408B, preventing fluid from moving through the channel 406B. At the same time, the decrease in pressure opens the first valve 408A, thereby permitting fluid to flow into the pump 400B through the channel 408A. This fluid enters the chamber 410 as the volume of the bubbles 502 decreases.

By cycling through the stages depicted in FIGS. 5A and 5B, fluid such as aqueous humor can be pumped through the pump 400B. Fluid is pushed out of the chamber 410 through the channel 406B in one stage and pulled into the chamber 410 through the channel 406A in the other stage. The cycling may be performed around at 1 hertz. In some embodiments, the cycling may be performed from about ½ hertz to about 5 hertz or more. Other frequencies may be used in other embodiments.

Figure 6A:
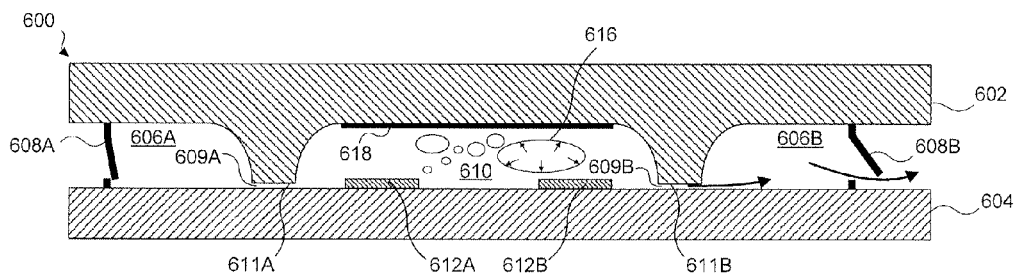
FIGS. 6A and 6B are cross-sectional views of another microfluidic pump in two stages according to exemplary aspects of the present disclosure.
Figure 6B:
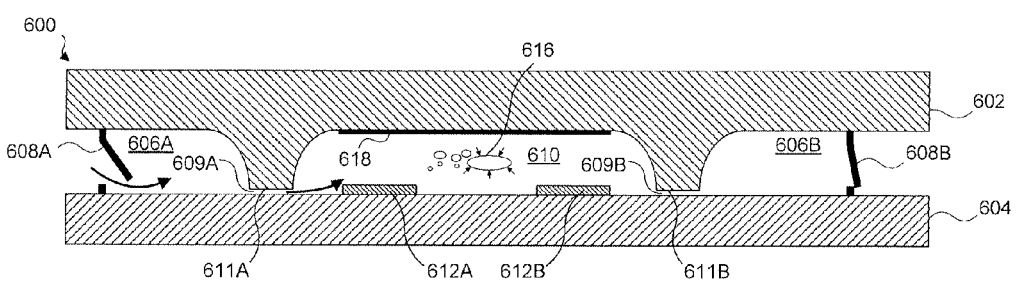

Referring now to FIGS. 6A and 6B, shown therein is an exemplary microfluidic pump 600 that is similar in some respects to the pumps 400A and 400B as discussed above. As seen in FIG. 6A, the pump 600 includes a first substrate 602 and a second substrate 604. The first and second substrates 602 and 604 may be made from glass, silicon, silicone, a polymeric material or other suitable material. In some embodiments, the first substrate 602 is made of a first material that is different from a second material of which the second substrate 604 is made. For example, the first substrate 602 may be made of glass while the second substrate 604 is made of a plastic material.

The pump 600 includes a channel 606, portions of which are shown in FIG. 6A. As shown, the channel 606A is accessed by a one-way valve 608A. The channel is coupled to proximal end 222 of the drainage tube 220. The other end of the channel 606A includes a gap 609A through which fluid can move from the channel 606A into a chamber 610. From the chamber 610, fluid may move through a second gap, gap 609B and thereby into the channel 606B. From the channel 606B, the fluid may flow through the one-way valve 608B into a drainage structure. The gaps 609A and 609B define the boundaries of the chamber 610 and are provided by protrusions 611A and 611B, respectively. The protrusions 611A and 611B are extensions of the material from which the substrate 602 is made and may be formed by an etch process. In other embodiments the protrusions 611A and 611B may be formed on the second substrate 604, while in others one protrusion is formed on the first substrate 602 and the other protrusion is formed on the second substrate 604. The protrusions 611A and 611B may be formed by an etching, milling, and/or deposition process. In some embodiments, the gaps 609A and 609B are provided by protrusions on the first substrate 602 and corresponding protrusions on the second substrate 604, such that the gaps 609A and 609B are positioned in the middle of the channels 606A and 606B.

Like the chamber 410 of FIGS. 4A and 4B, the chamber 610 includes an electrode 612A and an electrode 612B. As shown in FIG. 6A, when an electric potential is applied to the electrodes 612A and 612B within the chamber 610 to initiate an electrolysis process by which water molecules within the chamber 610 are separated by the presence of a direct electric current induced by the potential into hydrogen gas ($H_2$) and oxygen gas ($O_2$). The gaseous hydrogen and oxygen forms bubbles, like the bubble 616, within the chamber 610, and as these bubbles expand fluid is displaced out of the chamber 610. As the fluid is displaced, pressure within the chamber 610 and the channels 606A and 606B increases. The increase in pressure within the channel 606A closes the first valve 608A, preventing fluid from flowing out through the gap 609A and the channel 606A. At the same time, the increase in pressure within the channel 606B opens the valve 608B, allowing fluid to drain from the pump 600.

The gaps 609A and 609B provide hydrophilic channels that inhibit the bubbles, like bubble 616, from moving out of the chamber 610 either toward the channel 608A or toward the channel 608B. The gaps 609A and 609B may have the same dimensions or may have different dimensions. The height of the gap, or the separation between the substrates 602 and 604 in the gaps 609A and 609B, may range from about 1 micron to about 200 microns. The length of the gaps 609A and 609B, in various embodiments, ranges from about 5 microns to about 200 microns. This may be measured as the separation between the chamber 610 and the channel 606A or 606B at the lowest point of the protrusion 611A or 611B, respectively. In some embodiments, the width of the gaps 609A and 609B may be in a range from about 10 microns to about 400 microns. In some embodiments, the width of gaps 609A and 609B may be larger than a width of the channels 606A and 606B and the chamber 610. A larger width may decrease the fluidic resistance introduced by the gaps 609A and 609B.

While FIG. 6A illustrates a first stage of the pumping process enabled by the pump 600, FIG. 6B illustrates a second stage. When the electric potential is removed from the electrodes 612A and 612B, the bubbles begin to decrease in size. The bubbles, like bubble 616, may decrease as the hydrogen and oxygen gasses recombine into water at a recombination layer 618, shown in the illustrated embodiment on the upper surface of the chamber 610. The bubbles may also decrease as the gasses dissolve into the fluid in the chamber 610. As the volume of the bubbles decrease, the pressure within the chamber 610 decreases. This change in pressure closes the valve 608B and opens the valve 608A, drawing additional fluid through the channel 606A and the gap 609A into the chamber 610. By cycling between the two stages as shown in FIGS. 6A and 6B, fluid is moved by the pump 600. The fluid may be removed from an eye having an elevated intraocular pressure or from another pressurized site.

Figure 7A:
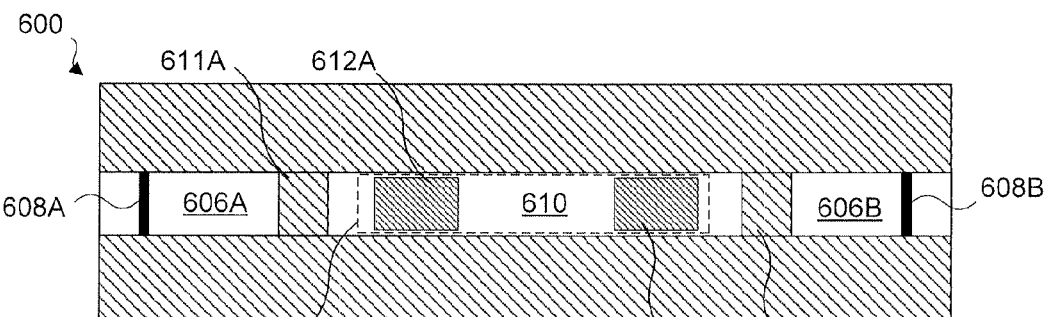
FIGS. 7A, 7B, and 7C are plan views of microfluidic pumps according to exemplary aspects of the present disclosure.
Figure 7B:
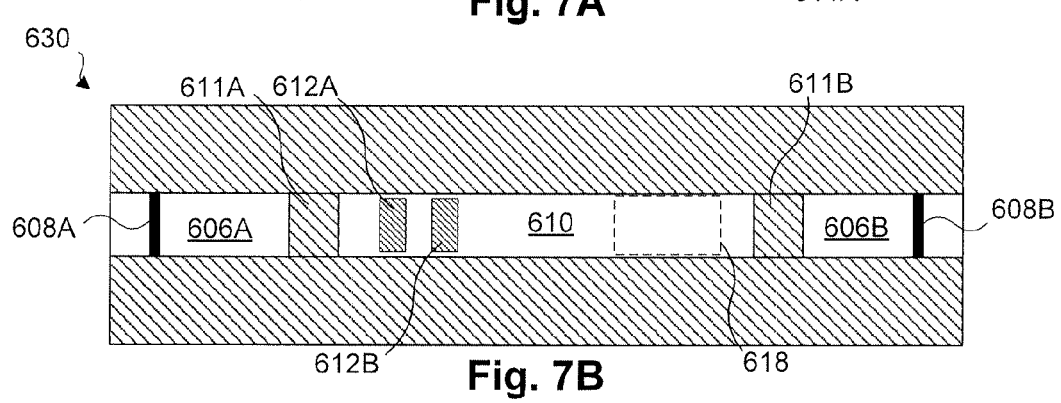
Figure 7C:
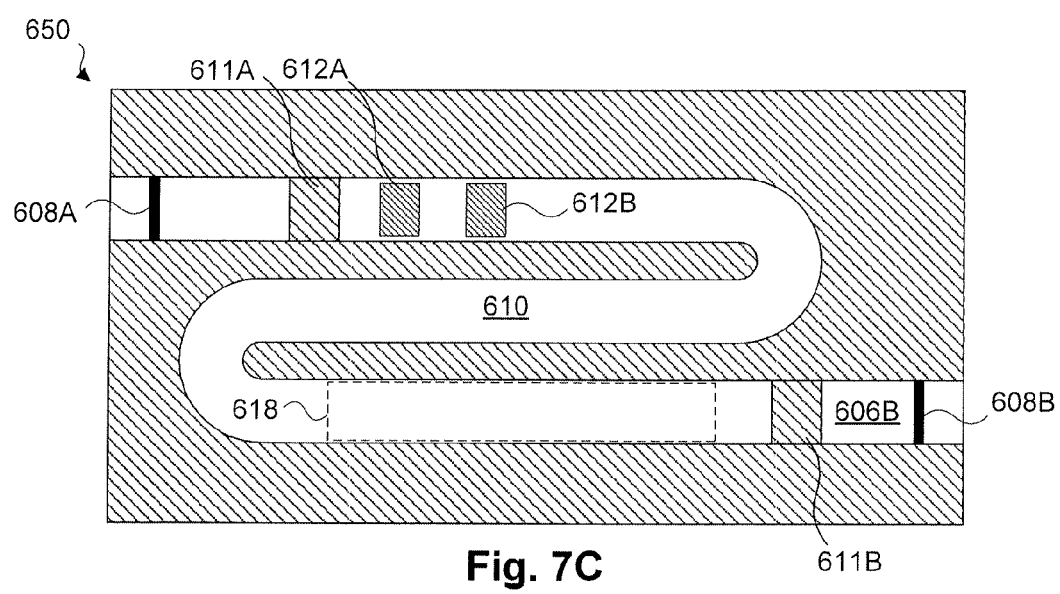

FIGS. 7A, 7B, and 7C are plan views that illustrate embodiments of the pump 600. FIGS. 7A-C provide additional perspective on some different embodiments of the shape of the channels 606A and 606B and the chamber 610. The configuration of pump 600 as shown in FIG. 7A includes a generally straight channel 606A, chamber 610, and channel 606B. The valve 608A is located in the channel 606A, while the valve 608B is in the channel 606B. The chamber 610 is configured between the channels 606A and 606B and includes the electrodes 612A and 612B on a bottom surface of the chamber 610 (as seen in FIGS. 6A and 6B the bottom surface is provided by the substrate 604). The recombination layer 618 is shown for reference as disposed on a top surface of the chamber, which is provided by the substrate 602. One electrode, electrode 612A, is disposed proximate the first protrusion 611A while the other electrode, electrode 612B, is disposed proximate the second protrusion 611B.

A different configuration is presented in FIG. 7B, which illustrates a plan view of a pump 630. The pump 630 includes many of the features described herein in connection with the pump 600. Thus, the pump 630 includes a pump path that includes the channels 608A and 608B and the chamber 610. Within the chamber 610, both of the electrodes 612A and 612B are positioned in a portion of the chamber 610 proximate the first protrusion 611A. The recombination layer 618 is positioned on an upper surface of the chamber 610 at an end of the chamber 610 proximate the second protrusion 611B. This configuration of the electrodes 612A and 612B and the recombination layer 618 may facilitate the formation of bubbles within the chamber 610 by increasing a separation between a bubble formation site and a recombination site.

Another configuration is presented in FIG. 7C, which illustrates a plan view of a pump 650. Like the pump 650 shares many of the features described herein in connection with pumps 630 and pump 600. The pump path of the pump 650 includes an inlet channel 606A and an outlet channel 606B with a chamber 610 therebetween. While the chambers 610 as seen in FIGS. 7A and 7B are generally straight, the chamber 610 of pump 650 has a serpentine shape. The serpentine shape provides a longer chamber 610, with more separation between the electrodes 612A and 612B and the recombination layer 610. This may further facilitate the formation of bubbles within the chamber 610. Additionally, the serpentine shape may allow the pump 650 to occupy smaller dimensions when positioned within the plate 210 of the device 200 of FIGS. 2 and 3. Other shapes may be used in other embodiments.

The systems and methods disclosed herein may be used to provide better performance for intraocular devices, such as increased control over drainage from the anterior chamber to regulate the IOP. This may be done by using microfluidic actuators in a microfluidic pump as described. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A microfluidic pump for implantation proximate an eye of a patient, the microfluidic pump comprising:
    a first substrate portion;
    a second substrate portion adjacent to the first substrate portion;
    a channel defined by and between the first and second substrate portions and having a proximal end and a distal end, the channel having a first valve in the proximal end and a second valve in the distal end; and
    a chamber having a bottom surface, side surfaces, and a top surface, wherein the top surface is provided by a rigid, liquid-permeable wall, the chamber producing a gas within the chamber that displaces fluid within the chamber and within the channel, the rigid, liquid-permeable wall being in fluid communication with the channel.

2. The microfluidic pump of claim 1, wherein the gas comprises $O_2$ and $H_2$.

3. The microfluidic pump of claim 1, wherein the wall is formed from an open-cell foam material.

4. The microfluidic pump of claim 1, wherein the chamber comprises a metal layer disposed on the side surfaces and on the bottom surface of the chamber such that the metal layer does not contact at least one of two electrodes within the chamber.

5. The microfluidic pump of claim 1, wherein the wall is formed from a hydrophilic material.

6. The microfluidic pump of claim 1, wherein the wall comprises a plurality of micro-pores.

7. The microfluidic pump of claim 1, wherein the first and second valves are check valves.

8. The microfluidic pump of claim 1, wherein the first and second substrate portions are made of glass.

9. The microfluidic pump of claim 1, further comprising a dividing member, the dividing member dividing the rigid, liquid-permeable wall into a first portion and a second portion and preventing fluid from passing through the channel without entering the chamber through the wall.

10. An intraocular device for regulating pressure within an eye of a patient, the intraocular device comprising:
    a plate having a cavity therein;
    a flexible tube having a proximal end and a distal end, the proximal end configured to insert into an anterior chamber of the eye and the distal end coupled to the plate; and
    a microfluidic pump configured within the cavity of the plate, the microfluidic pump comprising:
        a first substrate portion;
        a second substrate portion adjacent to the first substrate portion;
        a channel defined by and between the first and second substrate portions and in communication with the flexible tube; and
        a chamber having a bottom surface, side surfaces, and a top surface, wherein the top surface is provided by a liquid-permeable wall, a gas being produced within the chamber that displaces fluid from within the chamber into the channel, the rigid, liquid-permeable wall being in fluid communication with the channel.

11. The intraocular device of claim 10, wherein the channel comprises a first valve at a proximal end of the channel and a second valve at a distal end of the channel.

12. The intraocular device of claim 10, further comprising a pressure sensor coupled to the flexible tube to measure a pressure within an anterior chamber of the eye.

13. The intraocular device of claim 10, wherein the chamber is an electrolysis chamber that produces a gas from a liquid.

14. The intraocular device of claim 13, wherein the gas comprises $H_2$ and $O_2$ and the liquid is aqueous humor from the eye.

15. The intraocular device of claim 10, further comprising a dividing member, the dividing member dividing the wall into a first portion and a second portion and preventing fluid from passing through the channel without entering the chamber through the wall.

* * * * *